(12) United States Patent
Boland et al.

(10) Patent No.: US 9,034,589 B2
(45) Date of Patent: May 19, 2015

(54) MAGNETIC SEPARATION OF CELLS

(71) Applicants: Thomas Boland, El Paso, TX (US); Sylvia L. Natividad, El Paso, TX (US); Julio Rincon, Santa Teresa, NM (US)

(72) Inventors: Thomas Boland, El Paso, TX (US); Sylvia L. Natividad, El Paso, TX (US); Julio Rincon, Santa Teresa, NM (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 13/849,124

(22) Filed: Mar. 22, 2013

(65) Prior Publication Data
US 2014/0287437 A1  Sep. 25, 2014

(51) Int. Cl.
*G01N 33/53* (2006.01)
*G01N 33/555* (2006.01)
*G01N 33/569* (2006.01)

(52) U.S. Cl.
CPC .................. *G01N 33/56972* (2013.01)

(58) Field of Classification Search
None
See application file for complete search history.

(56) References Cited

U.S. PATENT DOCUMENTS

| | | | |
|---|---|---|---|
| 8,071,395 B2 * | 12/2011 | Davis et al. | 436/524 |
| 8,263,043 B2 | 9/2012 | Ahrens et al. | |
| 8,512,558 B2 * | 8/2013 | Meyer | 210/222 |
| 2010/0093052 A1 * | 4/2010 | Chalmers et al. | 435/173.9 |
| 2011/0294110 A1 | 12/2011 | Blair | |
| 2012/0295302 A1 * | 11/2012 | Lamish et al. | 435/39 |
| 2014/0093932 A1 * | 4/2014 | Murphy et al. | 435/173.4 |

OTHER PUBLICATIONS

Kim et al. Lab on Chip 9 (16( pp. 2313-2318) 2009.*
Williams et al. Abstract of American Chemical Society Mar. 23-27, 2003.*
Boland et al. Biotechnology Journal vol. 1, pp. 910-917, 2006.*

* cited by examiner

*Primary Examiner* — Robert B. Mondesi
*Assistant Examiner* — Khatol Shahnan Shah
(74) *Attorney, Agent, or Firm* — Luis M. Ortiz; Kermit D. Lopez; Ortiz & Lopez, PLLC

(57) ABSTRACT

An apparatus, system, and method for magnetic separation of cells are disclosed. By combining inkjet printing technology and magnetic labeling of cells, accurate cell counts are obtained using an optical microscope. Mouse CD4+ lymphocytes are attached to micron sized magnetic beads and printed through a modified, commercial inkjet printer. The labeled cells are then attached to a glass slide covering a permanent magnet. Cell counts can be obtained by use of regular and inverted optical microscopes and imaging software. The magnetically-labeled beads are collected for evaluation on a modified polymer coupon that is placed in front of a permanent magnet and the unlabeled cells fall into an excess container. Flow cytometry results verify the presence of the CD4+ protein on the LBRM-33 lymphocytes membrane. Protein-specific attachment of magnetic microspheres to the lymphocytes is utilized for sorting CD4+ lymphocytes.

19 Claims, 5 Drawing Sheets

FIG. 8

MAGNETIC SEPARATION OF CELLS

CROSS REFERENCE TO RELATED APPLICATIONS

This patent application claims the benefit under 35 U.S.C. §119(e) of U.S. Provisional Patent Application Ser. No. 61/614,149 filed on Mar. 22, 2012 and entitled "MAGNETIC CELL SEPARATION," which is hereby incorporated by reference in its entirety.

FIELD OF THE INVENTION

The disclosed embodiments relate to labeling of cells. The disclosed embodiments further relate to magnetic sorting and counting of cells. The disclosed embodiments also relate to protein-specific attachment of magnetic microspheres to CD4+ lymphocytes.

BACKGROUND

Separating a heterogeneous cell population based on cellular properties is a valuable analytic tool. Cell sorting devices separate cells from a suspension based on physical parameters of the cells of interest. When the cell population of interest does not differ significantly in size or density, current separation techniques are ineffectual.

The separation of target cells from the untargeted cells, and the maintenance of the membranes of target cells and untargeted cells, are particularly important in the early detection of HIV/AIDS and cancer, for example. One proposed way of detecting diseases such as HIV/AIDS, which specifically attacks CD4+ lymphocytes, involves inefficient equipment that can only be used in specialized clinics and tertiary medical centers. When one is infected with HIV but has not started treatment, the number of CD4+ cells decreases, A CD4+ lymphocyte count below 200 indicates serious immune damage and infection with HIV/AIDS. Normal counts are usually between 500 and 1600. CD4+ cell tests are usually reported as the number of cells in a cubic millimeter of blood, or $mm^3$.

There remains an unmet need for rapid and reliable magnetic separation CD4+ lymphocytes with high yield from a sample having a small concentration of such cells. Current separation techniques do not provide sufficient separated quantities of CD4+ lymphocytes to obtain a significant and reliable clinical, genetic, chemical or other analysis of the cells to indicate presence of diseases. Therefore, a need exists to magnetically label and separate target cells, such as CD4+ lymphocytes, to produce a concentration of the target cells for early detection of diseases.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the disclosed embodiments to provide for improved labeling of cells.

It is another aspect of the disclosed embodiments to provide for improved magnetic sorting and counting of cells.

It is a further aspect of the disclosed embodiments to provide for improved protein-specific attachment of magnetic microspheres to CD4+ lymphocytes.

The above and other aspects can be achieved as is now described. An apparatus, system, and method for magnetic separation of cells are disclosed. By combining inkjet printing technology and magnetic labeling of cells, accurate cell counts are obtained using an optical microscope. Mouse CD4+ lymphocytes are attached to micron sized magnetic beads and printed through a modified, commercial inkjet printer. The labeled cells are then attached to a glass slide covering a permanent magnet. Cell counts can be obtained by use of regular and inverted optical microscopes and imaging software. The magnetically-labeled beads are collected for evaluation on a modified polymer coupon that is placed in front of a permanent magnet and the unlabeled cells fall into an excess container. Flow cytometry results verify the presence of the CD4+ protein on the LBRM-33 lymphocytes membrane. Protein-specific attachment of magnetic microspheres to the lymphocytes is utilized for sorting CD4+ lymphocytes.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout, As used herein, the term "and/or" includes any and all combinations of one or more of the associated listed items.

The terminology used herein is for the purpose of describing particular embodiments only and is not intended to be limiting of the invention. As used herein, the singular forms "a","an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A technique to magnetically label and separate cells is disclosed. The technique can be performed in low-resource settings, at a decreased cost to the medical organization and the patient. By combining inkjet printing technology and magnetic labeling of cells it is possible to obtain accurate cell counts needing only a regular optical microscope. Mouse CD4+ lymphocytes are attached to micron-sized magnetic beads and printed through a modified, commercial inkjet printer. The labeled cells are attached to a glass slide covering a permanent magnet. The cell counts are obtained using regular and inverted optical microscopes and NIS-elements AR imaging software.

The disclosed analysis technique of flow cytometry is used to obtain a count of specified cells through immunofluorescent staining. The cell sorting process uses a modified thermal inkjet printer, originally manufactured to be light and portable. Thermal inkjet printing is desirable in cell sorting as it dependably handles delicate biological material, is quantifiable in terms of the sample and digital imaging, and provides an automated process that reduces the required skill level of the operator. Heterogeneous cell type mixtures with the same cell concentration as control samples in the modified printer are analyzed with flow cytometry for validation purposes and to obtain a reference standard. The biological ink used in the disclosed printing system comprises a cell mixture. The mixture can include micron-sized paramagnetic beads whose surfaces are functionalized with antibodies specific to one cell type. The magnetically-labeled beads are collected for evaluation on a modified glass microscope slide. The slide is placed in close proximity to a permanent magnet. Unlabeled cells fall into a gel-coated excess container.

Experimental Data

Mouse LBRM-33 (clone 4A2) lymphocytes were derived from radiation-induced T cell lymphoma (purchased from ATCC™ Manassas, Va.). The lymphocytes were cultured in suspension in RPMI1640 medium (Invitrogen™, Carlsbad, Calif.) with 0.05 mM 2-mercaptoethanol (Sigma-Aldrich Corp.™, ST. Louis, Mo.), 100 Uml penicillin, 100 Mg/ml streptomycin (Invitrogen™), and 10% fetal bovine serum (Atlanta Biologicals™, Lawrenceville, Ga.). Neonatal Human Dermal Fibroblasts (NHDF) were purchased from Lonza™ (Basel, Switzerland). The adherent cultures were maintained in Dulbecco's Modified Eagles Medium (DMEM) (Sigma-Aldrich™), 10% fetal bovine serum augmented by 1% antibiotic/antimycotic (Sigma-Aldrich™), and sodium bicarbonate (Sigma-Aldrich™) at pH 7.4. Phosphate buffered saline (PBS) (Invitrogen™) was used for cell washing. Trypsin (0.25% 1×) with 0.1% EDTA (Sigma-Aldrich™) was used for NHDF flask detachment during passaging. The fibroblasts and lymphocytes were cultured in a temperature controlled incubator (Fisher Scientific™, USA) with 5% $CO_2$ at 37° C.

Cell mixtures for the biological ink were prepared in a $1 \times 10^6 : 3 \times 10^6$ ratio of LBRM-33 lymphocytes to NHDF per milliliter. Cell count and viability were assessed by Trypan Blue exclusion. Fibroblast cells were detached using trypsin and harvested via centrifugation at 25° C. for 5 minutes and 1000 rpm. The LBRM-33 and fibroblast cell mixture was then centrifuged at 25° C. for 5 minutes at 1500 rpm. Pelleted cells were resuspended in PBS isolation buffer with Invitrogen™ Mouse CD4 Dynabcads® (Carlsbad, Calif.) to create a 1 mL sample of biological ink.

Invitrogen™ Mouse CD4 Dynabeads® were used to separate the LBRM 33 CD4+ lymphocytes from the fibroblasts. The Dynabeads® were polystyrene microspheres with a 4.5 um diameter and a magnetite core that are coated with the mouse CD4 antibody. Prior to attachment, 25 µL of the beads were washed in 1 mL of isolation buffer which consisted of PBS with 0.1% BSA and 2 mM EDTA. The beads were then resuspended in 1 mL of isolation buffer and added to pelleted cells, and mixed gently. The complete sample was allowed to incubate for 20 minutes at 8° C. with slow rotation.

Figure 1:
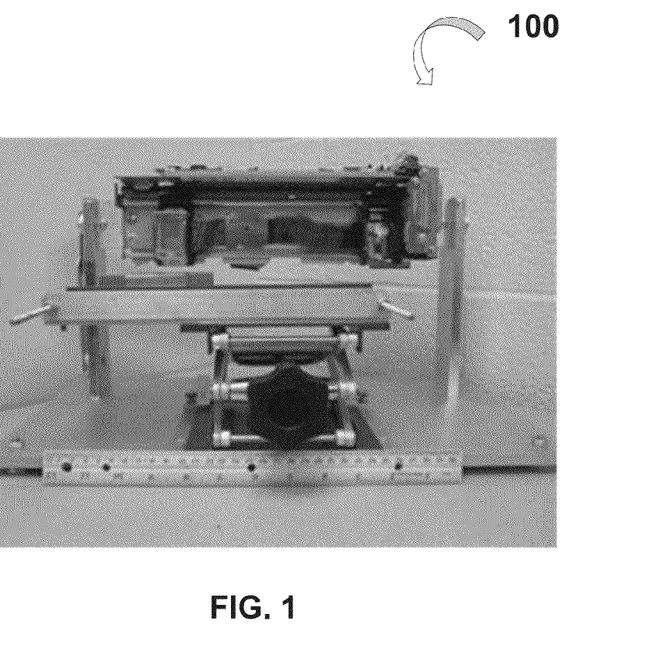
FIG. 1 illustrates an exemplary pictorial illustration of a printer to print and magnetically sort cells, according to a preferred embodiment.

FIG. 1 illustrates an exemplary pictorial illustration 100 of a modified Hewlett-Packard Deskjet 340 thermal inkjet printer to magnetically sort cells contained within the bio-ink in an automated process that is quantifiable by both sample size and digital imaging, according to embodiments. An exemplary Hewlett-Packard® Deskjet 340 thermal inkjet printer was modified to magnetically sort cells contained within the bio-ink in an automated process that is quantifiable by both sample size and digital imaging. Modifications to the printer include a lightweight, 6061 aluminum frame with a customized printing platform that holds the permanent magnet and excess container.

Figure 2A:
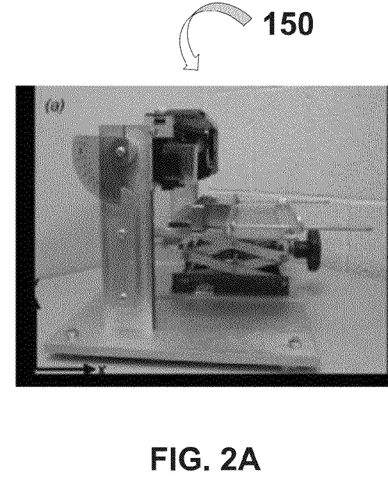
FIG. 2A illustrates an exemplary pictorial illustration of a modified thermal inkjet printer in a vertical printing position, according to an embodiment.
Figure 2B:
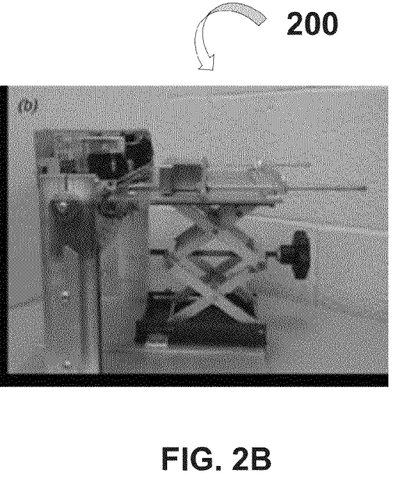
FIG. 2B illustrates an exemplary pictorial illustration of a modified thermal inkjet printer in a horizontal printing position, according to an embodiment.

FIG. 2A illustrates an exemplary pictorial illustration 150 of a modified thermal inkjet printer in a vertical printing position, according to embodiments. FIG. 2B illustrates an exemplary pictorial illustration 200 of a modified thermal inkjet printer in a horizontal printing position, according to embodiments. The printer is capable of printing at an arbitral angle between vertical and horizontal positions. The printing platform is adjustable in the ±x and ±y directions, which allows for flexibility in optimizing the distance between the modified ink cartridges to the permanent magnet. The permanent magnet configuration consists of two Neodymium rare-earth magnets. Both magnets are sintered $Nd_2Fe_{14}B$ Grade 42 with transverse magnetization and a Ni—Cu—Ni triple layer coating for corrosion resistance (Applied Magnets™, Plano, Tex., USA). The magnet to which the glass slide is mounted is 4"×1"×0.5" and has an approximate pull force of 110 pounds. The secondary magnet is 2"×1""1" with about 145 pounds of pull force. The excess container is a 60×15 mm petri dish filled with 3 mL 5% gelatin type A (MP Biomedicals™, Solon, Ohio) and 3 mL DMEM media augmented with 10% FBS.

The ink pens for the printer cartridge were modified to print cells, The original ink and a screen filter above the nozzle area were removed and the cartridge was thoroughly cleaned with ultrasonic agitation in deionized water for one minute. A 0.6 mL conical tube with openings on either end was then inserted into the nozzle pen area. The pen has 50 nozzles with 24 μm diameters and droplet volume of 85 pL. During a single firing of the nozzles, 50 pixels are printed. Multiplying this by the droplet volume gives an approximate printing volume of 0.43 μL for a single firing of all printer nozzles. During each printout for this study the printer fired 54 times so that the total printout volume was 23 μL. Different sample volumes of the homogenously dispersed bio-ink were tested in order to find the ideal printing capacity for cell sorting. The printed samples were viewed under a Nikon Eclipse Ti inverted optical microscope and 2560×1920 pixel images with 0.34 um/pixel resolution were taken using NIS-Elements™ AR imaging software (Melville, N.Y.).

A printing process for the modified printer was developed and optimized in the disclosed embodiments. Prior to printing, the silica microscope slides are thoroughly cleaned with Piranha Solution™ which is 3:1 sulfuric acid to 30% hydrogen peroxide to clean off any organic molecules that may be attached to the glass surface. Two surface treatments on the glass slides were tested in order to determine the ideal surface on which the labeled cells could be printed without any stray unlabeled cells adhering to the same area. The dean glass slides were coated with either Rain-X™ Original Glass Treatment (ITW Global Brands™, Houston, Tex.) or octadecyl trichloro silane (OTS) (ACROS Organics, N.J.) which created a hydrophobic coating. Some of the untreated and treated glass slides were also tested with a layer of 5% gelatin to determine its effect on the printed cells' viability. The treated and untreated glass slides, with or without gelatin, were printed upon in both vertical and horizontal printing positions with variations in the distance between the pen nozzle and magnet. The excess containers were replaced after each printout.

The images taken from the printed sample were used to evaluate cell sorting performance using Image J: Image Processing and Analysis in Java software, open-source software created by the National Institutes of Health (USA). The images were uploaded in TIFF format with a 100 μm marker used to scale the image. The images were then converted to 8-bit type and the edges of the cells were identified using the software. The threshold of the image was then adjusted and the size maxima were determined. The "particles" were then analyzed and the total cell count in the image was determined.

Flow cytometry using a Gallios Flow Cytometer (Beckman Coulter™, Miami, Fla.) was used to validate the thermal inkjet printing results. LBRM-33 cells (1×106) were stained with 0.1 μg anti-mouse CD3-FITC, 1 μg anti-mouse CD4-Pacific Blue, or 0.1 μg anti-mouse CD8-PE (all purchased from BD Biosciences, San Jose, Calif.) for 30 minutes.

Samples were fixed in 200 uL of 1% formaldehyde following staining (Sigma-Aldrich). Next, flow cytometry analyses were performed on 1×106 cells LBRM-33 with 3×106 fibroblast cells prepared at a 1:3 ratio and stained with 0.1 ug anti-mouse CD4-Pacific Blue and compared to unstained cells.

Results/Discussion

The horizontal printing position was found to be optimal for the printing process and was used in this study. In this position, the printing platform was raised as high as possible while still allowing the printer to remain at 90 and the magnet was approximately 3 cm from the pen nozzle, as illustrated in FIG. 2B. Printouts in the vertical position yielded very little cell collection on the glass slides and mixed cells were found in the excess containers. The surface preparation of the printing substrates was also integral to optimizing the printing process. The Piranha solution effectively cleaned the glass microscope slides and permitted even coating of OTS and Rain-X™.

After several printouts, the OTS was determined to be the best surface coating since it allowed the buffer solution to slide off the substrate with more ease while still capturing the magnetically labeled cells. The layer of gelatin on both treated and untreated glass slides was found to have no effect on the labeled cell's viability and its use was thus discontinued. A 10 μL printing volume was determined to be optimal since a single layer of distinct cells was printed on the slides, which is conducive to obtaining an accurate cell count as observed in FIG. 3A, where the LBRM-33 lymphocytes arc evenly distributed across the image.

Figure 3A:
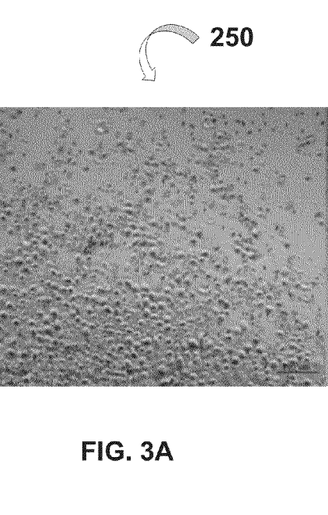
FIG. 3A illustrates an exemplary pictorial illustration of magnetically labeled cells collected on a slide, according to an embodiment.
Figure 3B:
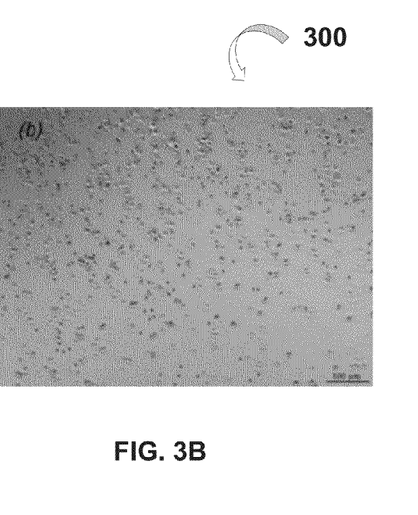
FIG. 3B illustrates an exemplary pictorial illustration of unmixed, magnetically labeled and printed cells, according to an embodiment.

FIG. 3A illustrates an exemplary pictorial illustration 250 of magnetically labeled LBRM-33 T cells collected on glass slide (1:3 mixed sample) and printed at 10 μL sample loading volume, according to embodiments. This figure, taken at 10× magnification, also shows the dynabeads attached to the backsides of the translucent cells. FIG. 3B illustrates an exemplary pictorial illustration 300 of unmixed, magnetically labeled LBRM-33 T cells and printed at a 10 μL sample loading volume, according to embodiments. For control test purposes, the cells in the image were compared with images of unmixed, labeled LBRM-33 lymphocytes, as illustrated in FIG. 3B, that were printed in the same manner.

Figure 4:
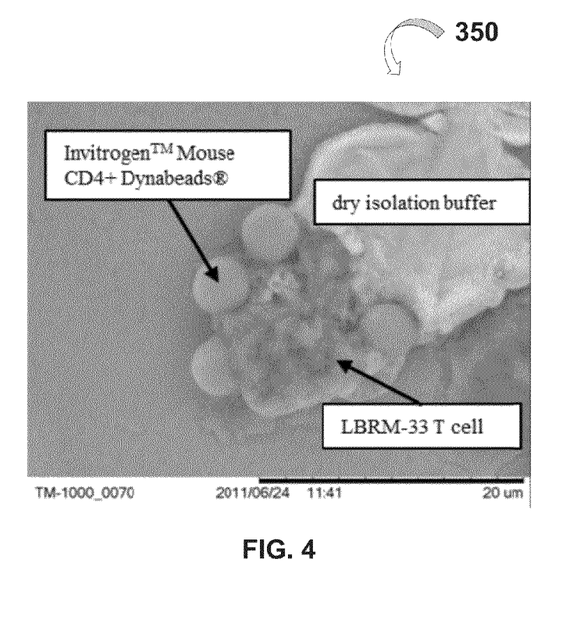
FIG. 4 illustrates an exemplary pictorial illustration of a SEM micrograph of bead attachment to cells, according to an embodiment.

FIG. 4 illustrates an exemplary pictorial illustration 350 of a SEM micrograph of bead attachment to cells taken 48 hours after printing, according to an embodiment. This demonstrates that dynabeads attach to the cell membrane and tend to gather on the backside of the cell as they are pulled by the magnetic field of the permanent magnet.

Figures 5A, 5B:
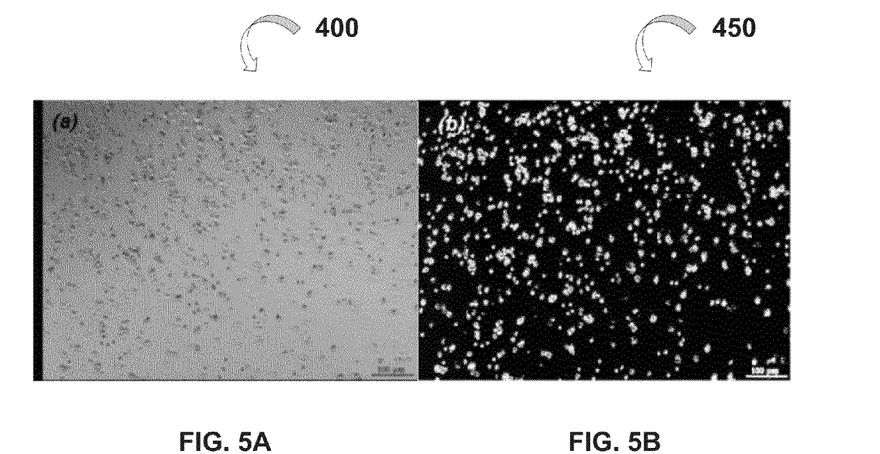
FIG. 5A illustrates an exemplary pictorial illustration of analyzed, unmixed, labeled lymphocytes, according to an embodiment.
FIG. 5B illustrates an exemplary pictorial illustration of analyzed, unmixed, labeled lymphocytes with a corresponding threshold, according to an embodiment.

FIG. 5A illustrates an exemplary pictorial illustration 400 of analyzed, unmixed, labeled LBRM-33 lymphocytes, according to an embodiment. To determine the volume contained within all image of the printed bio-ink sample at 10× magnification, a control sample consisting of only magnetically labeled LBRM-33 lymphocytes at a concentration of 1×106 cells/mL was printed. FIG. 5B illustrates an exemplary pictorial illustration 450 of analyzed, unmixed, labeled LBRM-33 lymphocytes with a corresponding threshold, according to an embodiment. FIG. 5B shows the images of the control sample with its corresponding adjusted threshold analysis in Image J that were used to obtain cell counts. A volume of 10 μL of the control sample was loaded into the printer pen for each printout. An average cell count of 1450 from the control sample printed images was obtained from Image 1. Thus, assuming a homogenous solution, there are about 10,000 cells in 10 μL of the sample which means the volume in a given printed image at 10× is about 1.5 μL. This sets a standard in which each printed image at 10× magnification of a sample containing 1×106 LBRM-33 lymphocytes/mL is approximately 1.5 μL and has about 1450 cells.

An average LBRM-33 T cell count of 1850 in the 10 μL printed images of the bio-ink was obtained from Image J analysis. When compared to the standard, this gives a concentration of about 12300 cells per 10-L and an overall concentration of 1.23×106 cells per mL. This was consistent with the 1×106 LBRM-33 lymphocytes/mL in the bio-ink mixture.

Figure 6A:
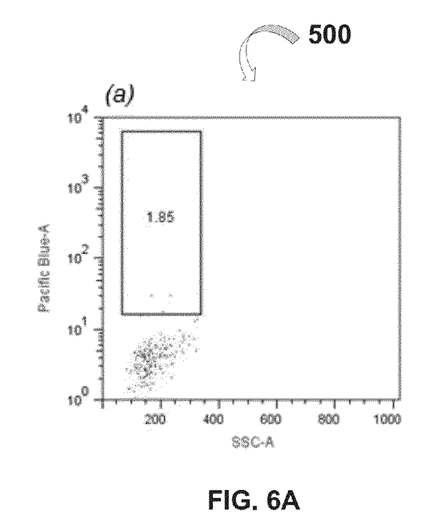
FIG. 6A illustrates an exemplary pictorial illustration of unstained flow cytometry results for lymphocytes, according to an embodiment.
Figure 6B:
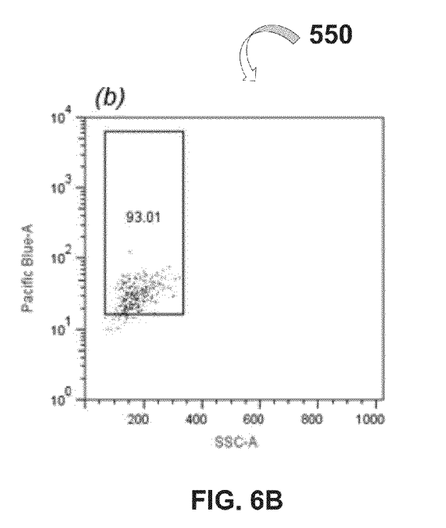
FIG. 6B illustrates an exemplary pictorial illustration of flow cytometry results for lymphocytes, according to an embodiment.

FIG. 6A illustrates an exemplary pictorial illustration 500 of unstained flow cytometry results for LBRM-33 lymphocyte, in accordance with the disclosed embodiments. FIG. 6B illustrates an exemplary pictorial illustration 550 of flow cytometry results for LBRM-33 lymphocyte, stained CD4 with 1 µg Pacific Blue, according to an embodiment. Initial testing with flow cytometry of the LBRM-33 (4A2) cell line verified the presence of CD4+ cells in approximately 93% of the population.

Figure 7A:
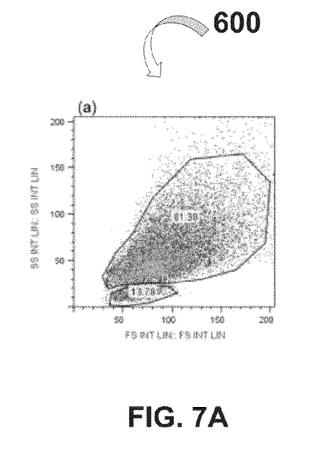
FIGS. 7A-7F illustrate exemplary pictorial illustrations of various stained and unstained populations of lymphocytes, according to embodiments.
Figure 7B:
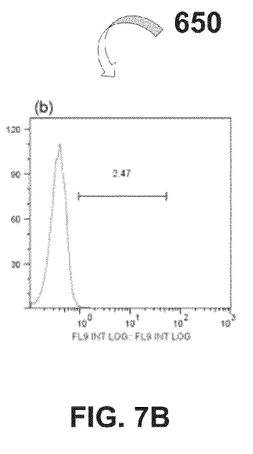
Figure 7C:
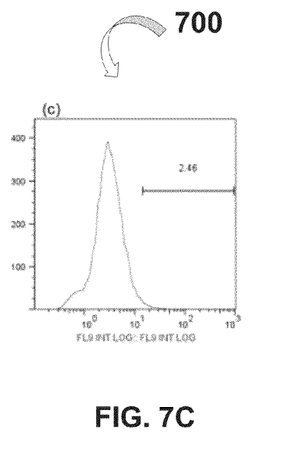
Figure 7D:
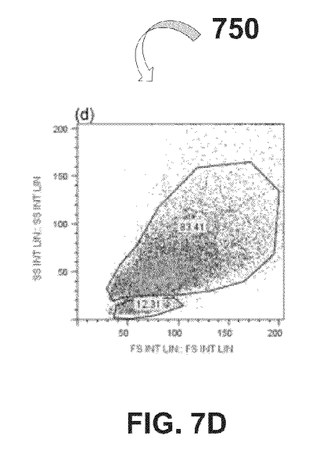
Figure 7E:
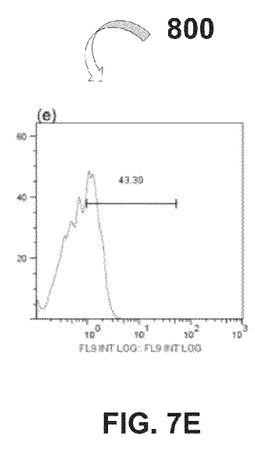

FIGS. 7A, 7B, 7C, 70, 7E, and IF illustrate exemplary pictorial illustrations 600, 650, 700, 750, 800, and 850, respectively, of various stained and unstained populations of LBRM-33 lymphocytes, according to embodiments. The overall assessment of the stained and unstained 1:3 cell LBRM-33 to fibroblast mixtures show expected, significant differences in size and granularity between the NI-IDF cells and the LBRM-33 lymphocytes as determined by forward scatter and side scatter analysis using flow cytometry. FIGS. 7A and 7D demonstrate this and show the gated positions of each cell type. The NHDF cells, in both the stained and unstained samples, are the larger and more abundant population which appears above the smaller and less granular LBRM-33 lymphocytes.

Figure 7F:
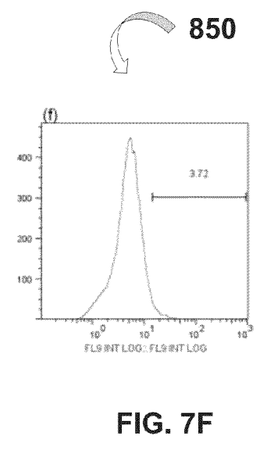

By forward scatter and side scatter analyses, fibroblasts composed 83.4% of the sample while the latter composed 12.3% of the population (as illustrated in FIGS. 7A and 7D). Furthermore, 43.3% of the cells gated as lymphocytes in the forward and side scatter plots were CD4+ (illustrated in FIG. 7E) as compared to unstained cells used as negative controls (illustrated in FIG. 7B). In contrast, the majority of the fibroblast-gated population was not CD4+ (illustrated in FIG. 7F) as compared to the unstained negative control fibroblast population (illustrated in FIG. 7C). FIGS. 7C and 7F illustrate a slight difference in the peak positions for the NHDF cells in the stained and unstained samples. Ideally, these peaks should be identical, but peak shifting may be due to nonspecific staining and the possibility of lymphocytes being included in the fibroblast gating.

Additional embodiments can include the following: printer modifications including software for cell sorting applications; printing lymphocytes while maintaining viability for cell sorting and cell counting applications; sorting of cells with magnetic beads, polymer coupons, excess container; counting sorted cells by fixating the cells; and, obtaining digital images, calculating the image volume, and using software to pick and enumerate the cells.

An inexpensive, portable alternative cell sorting alternative to flow cytometry for low resource settings is disclosed. This was achieved through the modification of a commercially available thermal inkjet printer and creation of an optimized printing process to sort cells. The modifications include low-cost materials such as a stand made out of a common aluminum alloy, commercially available neodymium magnets, and open source imaging software. The printing process was optimized to be simple and efficient so less training would be necessary to the operator in comparison to flow cytometry.

The biological ink used in this study was a 1:3 ratio of LBRM-33 lymphocytes to neonatal human dermal fibroblasts. An average cell count of about 1.2×106 LBRM-33 lymphocytes/mL was obtained from Image J analysis of mixed sample printouts based on the known concentration of control samples. Flow cytometry results verified the presence of the CD4+ protein on the LBRM-33 lymphocytes membrane along with demonstrating a significant size difference between the two cell types. This validated the use of protein-specific attachment of magnetic microspheres to the lymphocytes for cell sorting.

The following markers can be utilized in various embodiments of the disclosed cell separating and sorting techniques:

CD50 CD51 CD52 CD53 CD54 CD55 CD57 CD58 CD59 CDw60CD60a CD60b CD60c CD61 CD62E D62L CD62P CD63 CD64 CD65 CD65s CD66a CD66b CD66c CD66d CD66e CD66f CD67 CD68 CD69 CD70 CD71 CD72 CD73 CD74 CD75 CD75s CDw76 CD77 CDw78 CD79a CD79b CD80 CD81 CD82 CD83 CD84 CD85 CD85A 0085B CD85 C CD85D CD85E CD85F CD85G CD85H CD85I CD85J CD85K CD85L CD85M CD86 CD87 CD88 CD89 CD90 CD91 CDw92 CDw93 CD94 CD95 CD96 CD97 CD98 CD99 CD100 CD101 CD102 CD103 CD104 CD105 CD106 CD107a CD107b CD108 CD109 CD110 CD111 CD112 CD113 CD114 CD115 CD116 CD117 CD118 CDw119 CD120a CD120b CD121a CDw121b CD122 CD123 CD124 CDw125 CD126 CD127 CDw128a CD129 CD130 CDw131 CD132 CD133 CD134 CD135 CDw136 CDw137 CD138 CD139 CD140a CD140b CD141 CD142 CD143 CD144 CD146 CD147 CD148 CDw149 CD150 CD151 CD152 CD153 CD154 CD155 CD156a CD156b CD157 CD158 CD158a CD158b CD159a CD160 CD161 CD162 CD162R CD163 CD164 CD165 CD166 CD167a CD168 CD169 CD170 CD171 CD172a CD173 CD174 CD175 CD175s CD176 CD177 CD178 CD179a CD179b CD180 CD181 CD183 CD184 CD186 CD192 CD193 CD194 CD195 CD196 CDw197 CD198 CD199 CD200 CD201 CD202b CD203c CD204 CD205 CD206 CD207 CD208 CD209 CDw210 CD212 CD213a1 CD213a2 CD214 CDw217 CD218 CD220 CD221 CD222 CD223 CD224 CD225 CD226 CD227 CD228 CD229 CD230 CD231 CD232 CD233 CD234 CD235a CD235b CD235ab CD236 CD236R CD238 CD239 CD240 CE CD240 D CD240 DCE CD241 CD242 CD243.

Figure 8:
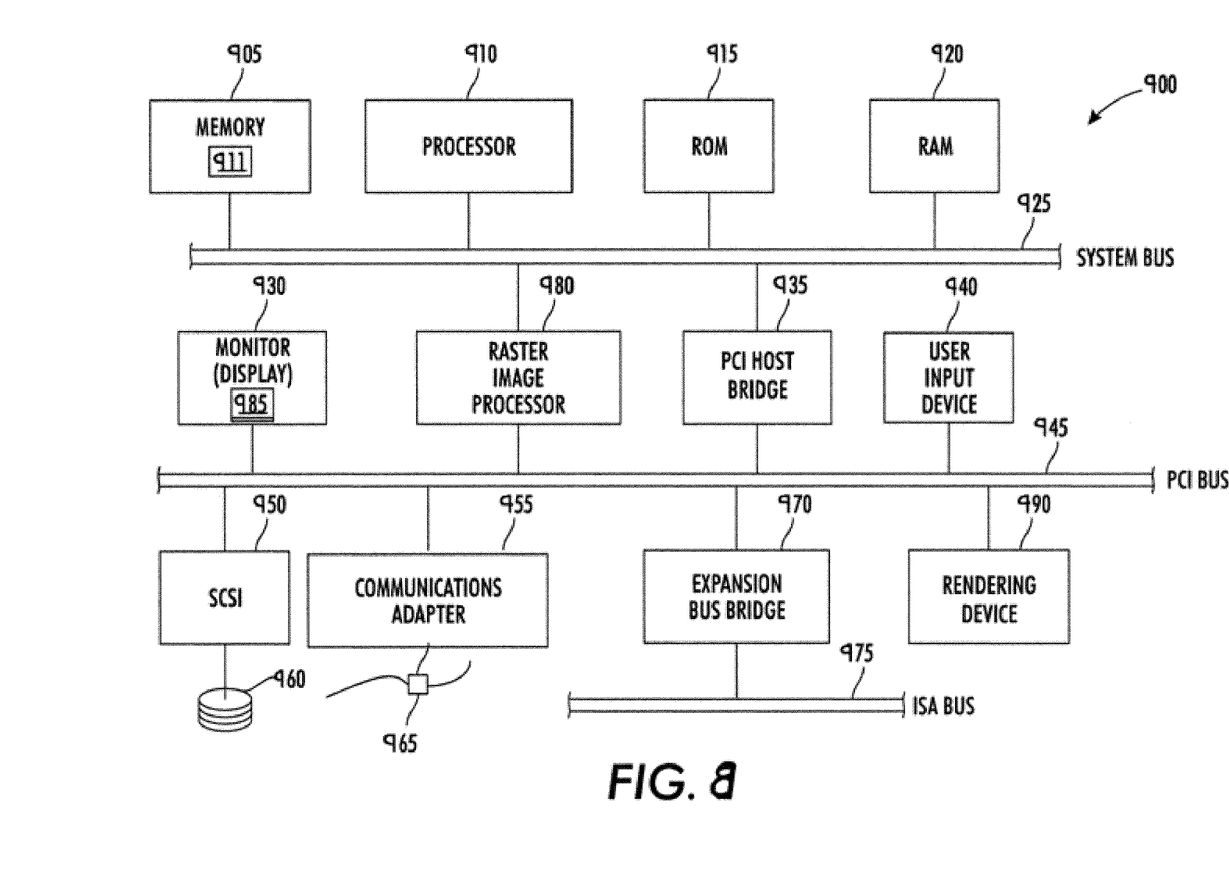
FIG. 8 illustrates a block diagram of a data-processing apparatus for magnetic labeling and separation of cells, according to an embodiment.

FIG. 8 illustrates a data-processing apparatus 900, according to an embodiment. Data processing apparatus 900 is utilized for accurately and reliable measuring joint angles. Data-processing apparatus 900 represents one of many possible data-processing and/or computing devices, which can be utilized in accordance with the disclosed embodiments. It can be appreciated that data-processing apparatus 900 and its components are presented for generally illustrative purposes only and do not constitute limiting features of the disclosed embodiments.

As depicted in FIG. 8, a memory 905, a processor (CPU) 910, a Read-Only memory (ROM) 915, and a Random-Access Memory (RAM) 920 are generally connected to a system bus 925 of data-processing apparatus 900, Memory 905 can be implemented as a ROM, RAM, a combination thereof, or simply a general memory unit. Magnetic labeling and sorting software module 911 includes software module in the form of routines and/or subroutines for carrying out features of the present invention and can be additionally stored within memory 905 and then retrieved and processed via processor 910 to perform a particular task, A user input device 940, such as a keyboard, mouse, or another pointing device, can be connected to PCI (Peripheral Component Interconnect) bus 945. Magnetic labeling and sorting software module 911 is adapted to provide a graphical user interface for processing the magnetic labeling and sorting. Processor 910 is adapted to process the magnetic labeling and sorting.

Data-process apparatus 900 can thus include CPU 910, ROM 915, RAM 920, and a rendering device 990 (e.g., printer, copier, scanner, xerography equipment, etc.), which are also coupled to a PCI (Peripheral Component Interconnect) local bus 945 of data-processing apparatus 900 through PCI host-bridge 935. The PCI Host Bridge 935 can provide a low latency path through which processor 910 may directly access PCI devices mapped anywhere within bus memory and/or input/output (I/O) address spaces. PCI Host Bridge 935 can also provide a high bandwidth path for allowing PCI devices to directly access RAM 920.

A communications adapter 955, a small computer system interface (SCSI) 950, a raster image processor (RIP) 980, and an expansion bus-bridge 970 can also be attached to PCI local bus 945. The communications adapter 955 can be utilized for connecting data-processing apparatus 900 to a network 965. SCSI 950 can be utilized to control high-speed SCSI disk drive 960. An expansion bus-bridge 970, such as a PCI-to-ISA bus bridge, may be utilized for coupling ISA bus 975 to PCI local bus 945. Note that PCI local bus 945 can further be connected to a monitor 930, which functions as a display (e.g., a video monitor) for displaying data and information for a user and also for interactively displaying a graphical user interface ("GUI").

As will be appreciated by one skilled in the art, one or more of the disclosed embodiments can be embodied as a method, system, or computer program usable medium or computer program product. Accordingly, the disclosed embodiments can in some instances take the form of an entire hardware embodiment, an entire software embodiment or an embodiment combining software and hardware aspects all generally referred to herein as a "module". Furthermore, the disclosed embodiments may take the form of a computer usable medium, computer program product, a computer-readable tangible storage device storing computer program code, said computer program code comprising program instructions executable by said processor on a computer-usable storage medium having computer-usable program code embodied in the medium. Any suitable computer readable medium may be utilized including hard disks, USB Flash Drives, DVDs, CD-ROMs, optical storage devices, magnetic storage devices, etc.

Based on the foregoing, it can be appreciated that a number of different embodiments, preferred and alternative, are disclosed herein. For example, in one embodiment, a method for cell sorting can be implemented. The method can include attaching protein-specific magnetic microspheres to cells; dispensing the cells and attached magnetic microspheres; and magnetically sorting the cells with attached magnetic microspheres. In some embodiments, magnetically sorting the cells with attached magnetic microspheres can include a step for magnetically separating the cells from unlabeled cells or fibroblasts. In other embodiments, the microspheres comprise an exterior surface, wherein the exterior surface is functionalized with antibodies specific to at least one cell type. In yet other embodiments, dispensing the cells and attaching the magnetic microspheres comprises printing the cells and attaching the magnetic microspheres via an inkjet printer, wherein the inkjet printer is modified to magnetically label and sort cells in a quantifiable and automated process. In some embodiments, the aforementioned cells can comprise either lymphocytes or CD4+ lymphocytes.

In another embodiment, a step can be implemented for sorting the cells and attach the magnetic microspheres on a polymer coupon slide, wherein the polymer coupon slide is placed in proximity to a magnet and the magnet attracts the magnetic microspheres and attach the cells, wherein magnetically-unlabeled cells fall into an excess container. In some embodiments, a step can be implemented for staining the sorted cells via immunofluorescent staining. In yet another embodiment, a step can be implemented for counting the sorted cells via flow cytometry. In another embodiment, a step can be implemented for collecting cells without attached magnetic microspheres. In yet another embodiment, a step can be implemented for verifying a presence of CD4+ protein or at least one marker on membranes of the cells.

Another embodiment discloses a system for cell sorting comprising a processor; a data bus coupled to the processor; and a computer-usable non-transitory storage medium embodying computer code, the computer-usable non-transitory storage medium being coupled to the data bus, the computer program code comprising program instructions executable by the processor, the program instructions comprising instructions to: attach protein-specific magnetic microspheres to cells; dispense the cells and attach the magnetic microspheres; and magnetically sort the cells with attached magnetic microspheres. Embodiments of the system include program instructions of the method.

In yet another embodiment, an apparatus for cell sorting is disclosed. The apparatus can include a plurality of protein-specific magnetic microspheres attached to cells; a rendering device for dispensing cells and attaching the magnetic microspheres; and a magnet for magnetically sorting the cells with attached magnetic microspheres. In some embodiments, magnetically sorting the cells with attached magnetic microspheres comprises magnetically separating the cells from unlabeled cells or fibroblasts. In another embodiment, the microspheres can comprise an exterior surface, wherein the exterior surface is functionalized with antibodies specific to at least one cell type. In another embodiment, the rendering device for dispensing the cells and attaching the magnetic microspheres can comprise printing the cells and attaching the magnetic microspheres via an inkjet printer, wherein the inkjet printer is modified to magnetically label and sort cells in a quantifiable and automated process. In yet another embodiment, the cells can comprise at least one of lymphocytes and CD4+ lymphocytes.

In an embodiment, the apparatus includes a polymer coupon slide for sorting the cells and attaching the magnetic microspheres, wherein the polymer coupon slide is placed in proximity to a magnet and the magnet attracts the magnetic microspheres and attached the cells, wherein magnetically-unlabeled cells fall into an excess container. In other embodiments, the apparatus includes immunofluorescent stain for staining the sorted cells; and a marker on membranes of the cells to verify a presence of CD4+ protein via flow cytometry.

It will be appreciated that variations of the above-disclosed and other features and functions, or alternatives thereof, may be desirably combined into many other different systems or applications. Furthermore, various presently unforeseen or unanticipated alternatives, modifications, variations or improvements therein may be subsequently made by those skilled in the art which are also intended to be encompassed by the following claims.

What is claimed is:
1. A cell sorting apparatus, comprising:
a plurality of protein-specific magnetic microspheres;
a printing device for dispensing cells via ink pens with nozzles and attaching said magnetic microspheres to cells, wherein said printing device comprises a modified printer that magnetically labels and sorts said cells in a quantifiable and automated process, said process comprising printing a volume of bio-ink and determining a volume of a printed cell image and obtaining a cell count in said printed bio-ink, wherein said modified printer prints said cells at an angle between vertical and horizontal positions; and
a magnet for magnetically sorting said cells with attached said magnetic microspheres, wherein said modified printer holds said magnet.

2. The apparatus of claim 1 wherein magnetically sorting said cells with attached said magnetic microspheres comprises magnetically separating said cells from unlabeled cells or fibroblasts.

3. The apparatus of claim 1 wherein said microspheres comprise an exterior surface, wherein said exterior surface of said microspheres are functionalized with antibodies specific to at least one cell type.

4. The apparatus of claim 1 wherein said rendering device comprises an inkjet printer, wherein said inkjet printer is modified to magnetically label and sort cells in a quantifiable and automated process.

5. The apparatus of claim 1 wherein said cells comprise at least one of lymphocytes and mouse CD4+ lymphocytes.

6. The apparatus of claim 1 further comprising:
a polymer coupon slide for sorting said cells and attached said magnetic microspheres, wherein said polymer coupon slide is placed in proximity to a magnet and said magnet attracts said magnetic microspheres and attached said cells, wherein magnetically-unlabeled cells fall into an excess container;
immunofluorescent stain for staining said sorted cells; and
a marker on membranes of said cells to verify a presence of CD4+ protein via flow cytometry.

7. A cell sorting apparatus, comprising:
a plurality of protein-specific magnetic microspheres;
a printing device comprising a thermal inkjet printer for dispensing cells via ink pens with nozzles and attaching said magnetic microspheres to cells, wherein said printing device comprises a modified printer that magnetically labels and sorts said cells in a quantifiable and automated process, said process comprising printing a volume of bio-ink and determining a volume of a printed cell image and obtaining a cell count in said printed bio-ink, wherein said modified printer prints said cells at an angle between vertical and horizontal positions;
a magnet for magnetically sorting said cells with attached said magnetic microspheres, wherein said modified printer holds said magnet; and
a digital imaging device for collecting a digital image of the magnetically sorted cells.

8. The apparatus of claim 7 further comprising:
a processor;
a data bus coupled to said processor; and
a computer-usable non-transitory storage medium embodying computer code, said computer-usable non-transitory storage medium being coupled to said data bus, said computer program code comprising instructions executable by said processor, said program instruction comprising instructions to:
evaluate said digital image of said magnetically sorted cells to calculate the image volume.

9. The apparatus of claim 8 further comprising:
computer program code comprising instructions executable by said processor, said program instruction comprising instructions to:
pick and enumerate said cells.

10. The apparatus of claim 9 wherein said microspheres comprise an exterior surface, wherein said exterior surface of said microspheres are functionalized with antibodies specific to at least one cell type.

11. The apparatus of claim 9 wherein said rendering device comprises an inkjet printer, wherein said inkjet printer is modified to magnetically label and sort cells in a quantifiable and automated process.

12. The apparatus of claim 9 wherein said cells comprise at least one of lymphocytes and mouse CD4+ lymphocytes.

13. The apparatus of claim 9 further comprising:
a polymer coupon slide for sorting said cells and attached said magnetic microspheres, wherein said polymer coupon slide is placed in proximity to a magnet and said magnet attracts said magnetic microspheres and attached said cells, wherein magnetically-unlabeled cells fall into an excess container;
immunofluorescent stain for staining said sorted cells; and
a marker on membranes of said cells to verify a presence of CD4+ protein via flow cytometry.

14. A cell sorting apparatus, comprising:
a plurality of protein-specific magnetic microspheres;
a printing device comprising a thermal inkjet printer for dispensing cells via ink pens with nozzles and attaching said magnetic microspheres to cells, wherein said printing device comprises a modified printer that magnetically labels and sorts said cells in a quantifiable and automated process, said process comprising printing a volume of bio-ink and determining a volume of a printed cell image and obtaining a cell count in said printed bio-ink, wherein said modified printer prints said cells at an angle between vertical and horizontal positions;
a magnet for magnetically sorting said cells with attached said magnetic microspheres, wherein said modified printer holds said magnet;
a digital imaging device for collecting a digital image of the magnetically sorted cells;
a processor;
a data bus coupled to said processor; and
a computer-usable non-transitory storage medium embodying computer code, said computer-usable non-transitory storage medium being coupled to said data bus, said computer program code comprising instructions executable by said processor, said program instruction comprising instructions to:
evaluate said digital image of said magnetically sorted cells to calculate the image volume.

15. The apparatus of claim 14 further comprising:
computer program code comprising instructions executable by said processor, said program instruction comprising instructions to:
pick and enumerate said cells.

16. The apparatus of claim 15 further comprising:
computer program code comprising instructions executable by said processor, said program instruction comprising instructions to:
count said sorted cells by fixating said cells.

17. The apparatus of claim 15 wherein said rendering device comprises an inkjet printer, wherein said inkjet printer is modified to magnetically label and sort cells in a quantifiable and automated process.

18. The apparatus of claim 15 wherein said cells comprise at least one of lymphocytes and mouse CD4+ lymphocytes.

19. The apparatus of claim 16 further comprising:
a polymer coupon slide for sorting said cells and attached said magnetic microspheres, wherein said polymer coupon slide is placed in proximity to a magnet and said magnet attracts said magnetic microspheres and attached said cells, wherein magnetically-unlabeled cells fall into an excess container;
immunofluorescent stain for staining said sorted cells; and
a marker on membranes of said cells to verify a presence of CD4+ protein via flow cytometry.

* * * * *